US012697028B2

(12) United States Patent
Laffoley et al.

(10) Patent No.: US 12,697,028 B2
(45) Date of Patent: Aug. 4, 2026

(54) CONTROL SYSTEM FOR SETTING ILLUMINATION POWER OF AN OPHTHALMIC IMAGING SYSTEM

(71) Applicant: Optos plc, Dunfermline (GB)

(72) Inventors: Brian Laffoley, Dunfermline (GB); Alan Williams, Dunfermline (GB)

(73) Assignee: Optos plc, Dunfermline (GB)

( * ) Notice: Subject to any disclaimer, the term of this patent is extended or adjusted under 35 U.S.C. 154(b) by 282 days.

(21) Appl. No.: 18/527,639

(22) Filed: Dec. 4, 2023

(65) Prior Publication Data

US 2024/0188822 A1 Jun. 13, 2024

(30) Foreign Application Priority Data

Dec. 7, 2022 (EP) ..................................... 22211929

(51) Int. Cl.
  *A61B 3/14* (2006.01)
  *A61B 3/00* (2006.01)
(52) U.S. Cl.
  CPC .............. *A61B 3/14* (2013.01); *A61B 3/0033* (2013.01)
(58) Field of Classification Search
  CPC ....... A61B 3/14; A61B 3/0033; A61B 3/0008; A61B 3/0025; A61B 3/102; A61B 3/12;
  (Continued)

(56) References Cited

U.S. PATENT DOCUMENTS

| | | | |
|---|---|---|---|
| 8,636,362 B2 * | 1/2014 | Iwanaga ................... | A61B 3/14 |
| | | | 351/206 |
| 2005/0041207 A1 * | 2/2005 | Miller ..................... | A61B 3/156 |
| | | | 351/200 |
| 2007/0201003 A1 * | 8/2007 | Rankin .............. | G03B 15/0457 |
| | | | 352/29 |
| 2009/0055784 A1 | 2/2009 | Izumi et al. | |

(Continued)

FOREIGN PATENT DOCUMENTS

| | | | |
|---|---|---|---|
| CN | 205265961 U | 5/2016 | |
| EP | 1696328 A2 | 8/2006 | |
| EP | 2967315 B1 * | 7/2022 | ........... A61B 3/0083 |

OTHER PUBLICATIONS

European Search Report for EP Patent Application No. 22211929.9, Issued on May 19, 2023, 11 pages.

(Continued)

*Primary Examiner* — Mohammed A Hasan
(74) *Attorney, Agent, or Firm* — Faegre Drinker Biddle & Reath LLP

(57) ABSTRACT

There is provided a control system for controlling two or more illuminates of a multi-modality ophthalmic imaging system that are arranged to generate light for imaging an eye, the control system comprising: a processor which selects, from the illuminates and based on a selected imaging modality of the ophthalmic imaging system, one or more (Continued)

illuminates that are to be used to image the eye, and to generate an input signal identifying the selected one or more illuminates. The control system further comprises a logic block, which receives the input signal and comprises logic that determines a respective operating power for each illuminate of the selected one or more illuminates, based on the received input signal. The logic block also generates a respective control signal for each illuminate of the selected one or more illuminates, each control signal indicating the respective operating power determined for the respective illuminate.

11 Claims, 7 Drawing Sheets

(58) Field of Classification Search
CPC .... H05B 47/165; H05B 47/155; H05B 47/17; G06V 40/19
USPC ........................................................ 351/206
See application file for complete search history.

(56) References Cited

U.S. PATENT DOCUMENTS

| | | | |
|---|---|---|---|
| 2016/0000324 A1 | 1/2016 | Rege et al. | |
| 2016/0015264 A1 | 1/2016 | Pankajakshan et al. | |
| 2016/0067087 A1* | 3/2016 | Tedford | A61N 5/0624 |
| | | | 606/4 |
| 2016/0073878 A1 | 3/2016 | Su et al. | |
| 2016/0331230 A1 | 11/2016 | Liu et al. | |
| 2017/0027444 A1 | 2/2017 | Rege et al. | |
| 2018/0062344 A1* | 3/2018 | Smith | G01J 1/4257 |
| 2019/0142636 A1* | 5/2019 | Tedford | A61N 5/0616 |
| | | | 606/4 |
| 2020/0149864 A1 | 5/2020 | Kinrot et al. | |
| 2021/0045672 A1 | 2/2021 | Jia et al. | |

OTHER PUBLICATIONS

Examination Report issued in related application EP 22211929.9, Dec. 12, 2025, 7 pages.

* cited by examiner

| Imaging modality | Selection of illuminate(s) | Power of Red Laser | Power of Green Laser | Power of Blue Laser |
|---|---|---|---|---|
| 1 | Red only | HIGH | ZERO | ZERO |
| 2 | Green only | ZERO | HIGH | ZERO |
| 3 | Blue only | ZERO | ZERO | HIGH |
| 4 | Red and Green | HIGH | HIGH | ZERO |
| 5 | Red and Blue | LOW | ZERO | LOW |
| 6 | Green and Blue | ZERO | LOW | HIGH |
| 7 | Red, Green and Blue | LOW | LOW | LOW |

Figure 3

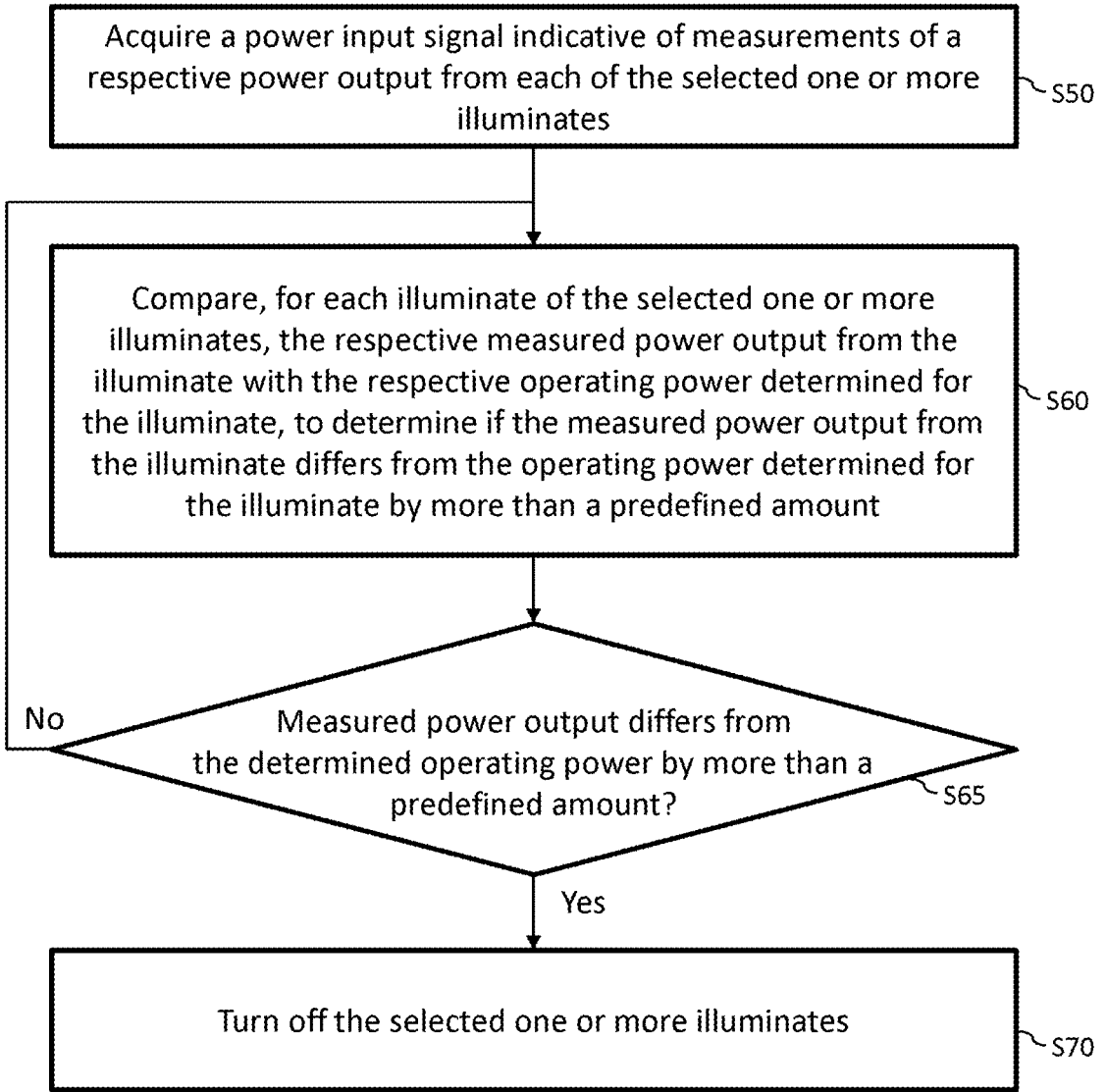

Acquire a power input signal indicative of measurements of a respective power output from each of the selected one or more illuminates ~S50

Compare, for each illuminate of the selected one or more illuminates, the respective measured power output from the illuminate with the respective operating power determined for the illuminate, to determine if the measured power output from the illuminate differs from the operating power determined for the illuminate by more than a predefined amount ~S60

No    Measured power output differs from the determined operating power by more than a predefined amount? ~S65

Yes

Turn off the selected one or more illuminates ~S70

Figure 6

CONTROL SYSTEM FOR SETTING ILLUMINATION POWER OF AN OPHTHALMIC IMAGING SYSTEM

FIELD

The present disclosure relates to control systems for controlling illuminates within an ophthalmic imaging system, and more particularly but not exclusively, to a control system which is arranged to control the power level of illuminates within an ophthalmic imaging system based on a selected imaging modality.

BACKGROUND

Ophthalmic imaging devices are widely used to image a patient's eye in order to assess the health of the eye. Some modern ophthalmic imaging devices can operate in multiple imaging modalities such that the clinician can select an imaging modality that is most suited to imaging a given region or disease in the patient's eye. Each imaging modality allows the ophthalmic imaging system to acquire a different type of ophthalmic image, which helps the clinician to acquire images containing information most appropriate for diagnosing ocular disease.

For example, in a scanning laser ophthalmoscope (SLO), a colour imaging modality may be used to acquire a fundus image of a patient's ocular fundus, including a portion of the retina. In this imaging modality, a combination of red, green and blue laser light may be delivered to the patient's eye to acquire images of the ocular fundus. Infrared retinal imaging is another example of an imaging modality that may be used to image a patient's eye. Infrared imaging delivers light from an infrared laser to the patient's eye, and may be used to detect retinal pathologies such as intraretinal fluid or retinal pigment epithelium tear. Another example of an imaging modality is optical coherence tomography (OCT). OCT imaging is a non-invasive imaging technique that allows a clinician to acquire cross-sectional and/or three-dimensional images of tissue.

In order to operate in the various imaging modalities provided in a multi-modality ophthalmic imaging device, a combination of illuminates may need to be operated to deliver light of the required wavelengths to the patient's eye for the selected imaging modality. Furthermore, the power of each illuminate must be set correctly for a given imaging modality to ensure the correct power of light is being delivered to the patient's eye. There is therefore a requirement for a control system which can ensure that the correct combination of wavelengths and power of light is delivered to the patient's eye, in accordance with the requirements of each imaging modality.

SUMMARY

In a broad sense examples embodiments of the invention relate to a control system for automatically determining and setting an operating power of each illuminate within an ophthalmic imaging system that is required for a selected imaging modality.

There is provided, in accordance with a first example aspect herein, a control system for controlling two or more illuminates of a multi-modality ophthalmic imaging system that are arranged to generate light for imaging an eye. The control system comprises a processor arranged to select, from the two or more illuminates and based on a selected imaging modality of the ophthalmic imaging system, one or more illuminates that are to be used to image the eye, and to generate an input signal identifying the selected one or more illuminates. The control system further comprises a logic block arranged to receive the input signal from the processor, wherein the logic block comprises logic arranged to determine a respective operating power for each illuminate of the selected one or more illuminates, based on the received input signal. The logic block is further arranged to generate a respective control signal for each illuminate of the selected one or more illuminates, wherein each control signal indicates the respective operating power determined for the respective illuminate.

In an example embodiment, the logic in the logic block may comprise hardwired logic arranged to receive the input signal from the processor and determine the respective operating power for each illuminate of the selected one or more illuminates, based on the received input signal. In the example embodiment, the logic block may additionally or alternatively comprise two or more inputs coupled to the processor, wherein each input corresponds to a respective illuminate of the two or more illuminates within the ophthalmic imaging system, and wherein the input signal generated by the processor identifies the selected one or more illuminates by comprising a respective signal transmitted to each of one or more inputs of the logic block that correspond to the selected one or more illuminates.

In the control system of the first example aspect or any of its embodiments or variants thereof set out above, the logic block may, in accordance with a further example embodiment, comprise, for each illuminate within the ophthalmic imaging system, a respective two or more outputs arranged to output control signals for controlling an operating power of the illuminate, and wherein a control signal output from each output of the two or more outputs is arranged to set an operating power of the illuminate to a respective power level. In this case, the logic block may comprise, for each illuminate within the ophthalmic imaging system, a respective first output and a respective second output, and wherein a control signal output from the respective first output is arranged to set an operating power of the illuminate to a first power level (e.g. a pre-set low power level), and a control signal output from the respective second output is arranged to set an operating power of the illuminate to a second power level (e.g. a pre-set high power level) which is higher than the first power level. The logic block may set the operating power of each illuminate of the selected one or more illuminates by either providing an input to the illuminate via the respective first output or the respective second output. Providing no input to an illuminate may cause the illuminate to be set of an off (inactive) state, with the illuminate not outputting any light.

In the control system of the first example aspect or any of its embodiments or variants thereof set out above, the control system may further comprise: a power monitor arranged to measure a respective power output from each of the two or more illuminates within the ophthalmic imaging system, and to generate a power input signal indicative of the measured power outputs; and an electronic safety system comprising, which comprises one or more first inputs arranged to receive the power input signal from the power monitor, one or more second inputs arranged to receive, from the logic block, the respective control signal generated for each illuminate of the selected one or more illuminates, and a controller arranged to compare, for each illuminate of the selected one or more illuminates, the respective measured power output from the illuminate with the respective operating power determined for the illuminate, to determine if the measured power output from the illuminate differs from the operating power determined for the illuminate by more than a predefined amount.

The controller may further be arranged, in response to determining that the measured power output from an illuminate of the selected one or more illuminates differs from the operating power determined for the illuminate by more than the predefined amount, to generate a control signal to turn the illuminate off. This control signal may, for example, be in the form of a trip signal for disconnecting a power supply to the illuminate. The control signal may alternatively be in the form a signal which causes a shutter mechanism to close an optical shutter and thus prevent light from the illuminate being delivered to the patient's eye. The electronic safety system may thus introduce a layer of redundancy in the control system by providing an additional check to ensure that the selected one or more illuminates within the ophthalmic imaging system are operating as expected.

The power monitor may comprise a photodiode power sensor or a thermal power sensor arranged to measure a respective power output from each of the two or more illuminates within the ophthalmic imaging system. The electronic safety system may comprise a controller, logic hardware or processor arranged to make the comparison. The controller of the electronic safety system may comprise hard-wired logic or processor arranged to execute a computer program stored in a memory, in either case being arranged to make the above-mentioned functions of the controller.

There is also provided, in accordance with a second example aspect herein, a multi-modality ophthalmic imaging system comprising two or more illuminates that are arranged to generate light for imaging an eye, and the control system of the first example aspect or any of its embodiments or variants thereof set out above, which is arranged to control the two or more illuminates.

There is also provided, in accordance with a third example aspect herein, a method of controlling two or more illuminates of a multi-modality ophthalmic imaging system that are arranged to generate light for imaging an eye. The method comprises: acquiring an indication of an imaging modality in which the multi-modality ophthalmic imaging system is to image the eye; selecting (by a processor executing computer program instructions, for example), from the two or more illuminates and based on the acquired indication of the imaging modality, one or more illuminates that are to be used to image the eye; determining (preferably by a hard-wired logic) a respective operating power for each illuminate of the selected one or more illuminates, based on the selection of one or more illuminates; and generating a respective control signal for each illuminate of the selected one or more illuminates, wherein each control signal indicates the respective operating power determined for the respective illuminate.

The method set out above may further comprise: acquiring a power input signal indicative of measurements of a respective power output from each of the selected one or more illuminates; comparing, for each illuminate of the selected one or more illuminates, the respective measured power output from the illuminate with the respective operating power determined for the illuminate, to determine if the measured power output from the illuminate differs from the operating power determined for the illuminate by more than a predefined amount; and in response to determining that, for at least one illuminate of the selected one or more illuminates, the measured power output from the illuminate differs from the operating power determined for the illuminate by more than the predefined amount, turning off the selected one or more illuminates (by outputting a trip signal for disconnecting a power supply to the selected one or more illuminates, or otherwise).

Within the scope of this application it is expressly intended that the various aspects, embodiments, examples and alternatives set out in the preceding paragraphs and/or in the following description and drawings, and in particular the individual features thereof, may be taken independently or in any combination. That is, all embodiments and/or features of any embodiment can be combined in any way and/or combination, unless such features are incompatible.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

FIG. 3 is a table showing operating powers of illuminates in the light source for seven example imaging modalities of the ophthalmic imaging system of FIG. 1.

FIG. 6 is a flow chart which is an optional continuation of the flow chart of FIG. 5, and illustrates operations performed by an electronic safety system of an example embodiment.

DETAILED DESCRIPTION

Figure 1:
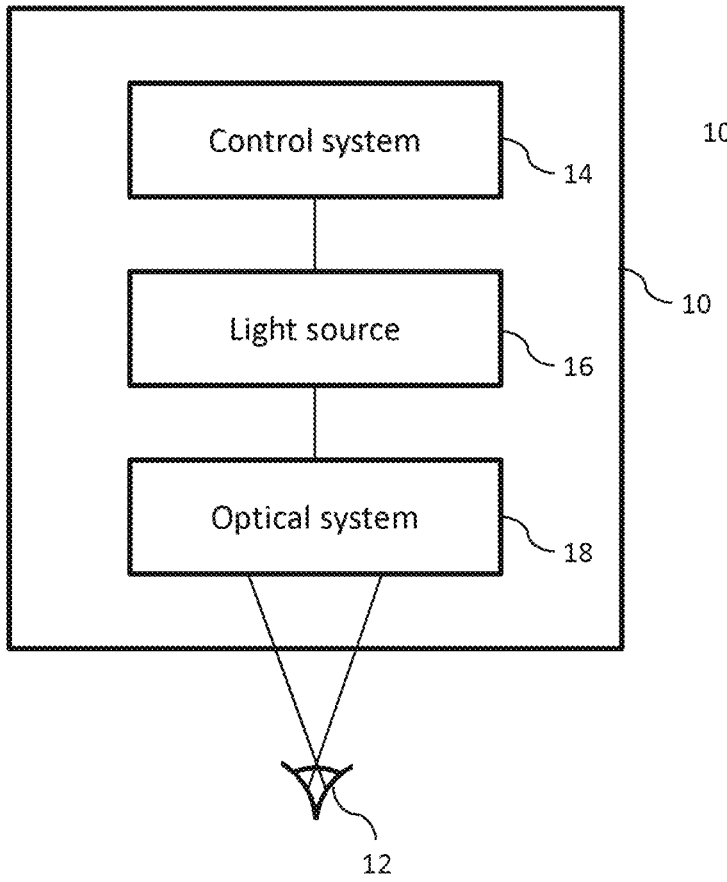
FIG. 1 is a schematic diagram of an ophthalmic imaging system having a light source suitable for use with a control system according to example embodiments herein.

There is described in the following a control system in accordance with an example embodiment, which is arranged to control two or more illuminates of a multi-modality ophthalmic imaging system that are arranged to generate light for imaging an eye. The control system comprises a processor arranged to select, from the two or more illuminates and based on a selected imaging modality of the ophthalmic imaging system, one or more illuminates that are to be used to image the eye, and to generate an input signal identifying the selected one or more illuminates. The control system further comprises a logic block arranged to receive the input signal from the processor, wherein the logic block comprises logic arranged to determine a respective operating power for each illuminate of the selected one or more illuminates, based on the received input signal. The logic block is further arranged to generate a respective control signal for each illuminate of the selected one or more illuminates, wherein each control signal indicates the respective operating power determined for the respective illuminate.

In this example embodiment, the operating power of each illuminate in the ophthalmic imaging system (e.g. the power consumed by the illuminate or the optical power output of the illuminate) is determined by logic hardware which is located within a logic block and dedicated to this task. The dedicated logic hardware, which does not comprise a processor arranged to execute a computer program stored in a storage device (memory), is more robust and stable than software running on a processor, and, as such, may improve the reliability with which the operating power of the selected illuminates within the ophthalmic imaging system can be determined and set. Furthermore, if the software running on the processor, which controls the operation of the multi-modality ophthalmic imaging system, were to glitch or crash, the isolation of the power control logic (for setting the operating power of the one or more selected illuminates) from the remaining logic implemented in the processor, and the implementation of the power control logic in a logic block form instead (which is dedicated to the power control logic, i.e. arranged to implement the power control logic only), as described herein, may reduce the risk of potentially harmful powers of illumination being delivered to the patient's eye. Splitting the determination of operating power levels away from the processor to the logic block in this way may help to improve the reliability of the control system.

The logic in the logic block may comprise hardwired logic. Alternatively, the logic in the logic block may comprise a programmable logic array. The logic may be arranged to determine if the selection of one or more illuminates identified by the input signal from the processor is a valid selection. If the identified selection of one or more illuminates is an invalid selection or a selection that is not programmed in the logic, the logic block may be arranged to generate a control signal that does not turn on any of the one or more illuminates identified by the input signals.

To place example embodiments in a suitable context, reference will now be made to FIG. 1, which schematically shows an ophthalmic imaging system 10 for acquiring ophthalmic images of a patient's eye 12. The ophthalmic imaging system 10 comprises a control system 14 operatively coupled to a light source (which may also be referred to as an illumination module) 16 within the ophthalmic imaging system 10. The ophthalmic imaging system 10 may, as in the present example embodiment, further comprise an optical system 18, which is optically coupled to the light source 16 and arranged to convey light from the light source 16 to the patient's eye 12. The ophthalmic imaging system 10 may further comprise one or more photodetectors (not shown) for detecting light reflected by the patient's eye 12, and a signal processing device arranged to generate ophthalmic images based on an output of the photodetector(s).

The ophthalmic imaging system 10 is a multi-modality imaging system, in which a user of the ophthalmic imaging system 10 can select one of a plurality of imaging modalities to image the patient's eye 12. The light source 16 may comprise two or more illuminates (in other words, light sources) that are operable independently of each other such that a single one of the illuminates, or any combination of two of more of the illuminates, may be selected to provide illumination for the imaging performed by the ophthalmic imaging system 10, the selection depending on the selected imaging modality of the ophthalmic imaging system 10. Furthermore, the illuminates within the light source 16 are controllable such that the output power of each illuminate can be independently set by the control system 14.

The control system 14 is arranged to generate, based on a selected imaging modality of the ophthalmic imaging system 10 and for each illuminate that is required for the selected imaging modality, a respective control signal indicating a respective operating power to be set for the illuminate. The structure of the control system 14 is described in more detail below, with reference to FIG. 2.

The light source 16 receives the control signal(s) output from the control system 14 and the selected one or more illuminates within the light source 16 are illuminated (i.e. turned on, to emit light), in accordance with the selected imaging modality. Light is output from the light source 16, for example in the form of a beam comprising light from the selected one or more illuminates, as in the present example embodiment. The light beam from the light source 16 is conveyed to the optical system 18. The optical system 18 may comprise a scanning system, which comprises one or more scanning mirrors arranged to scan the light beam from the light source 16 across a region of the eye 12, such as a portion of the retina of the eye 12, and to collected return light from the scanned region of the eye 12. The return light (or a light based on the return light, for example an interference light resulting from an interference between the return light and a reference light, as in the case of an OCT imaging modality being used by the ophthalmic imaging system 10) undergoes photoelectric conversion by the one or more photodetectors of the ophthalmic imaging system 10 to generate an electrical signal. The electrical signal is processed by the signal processing hardware of the ophthalmic imaging system 10 mentioned above to generate an image of the scanned portion of the eye 12. The scanning system may be a scanning galvanometer system or any other scanning system suitable for scanning the light beam across an area of the patient's eye 12. Furthermore, although the scanning system may, as in the present example embodiment, be a point-scanning system, the optical system 18 may alternatively comprise a line-scanning system arranged to provide line-field illumination of the scanned region of the eye 12. As a further alternative, the optical system 18 of another example embodiment may comprise, instead of a scanning system (of one of the forms set out above, for example), an optical arrangement that provides full-field illumination of an imaged region of the eye 12.

Figure 2:
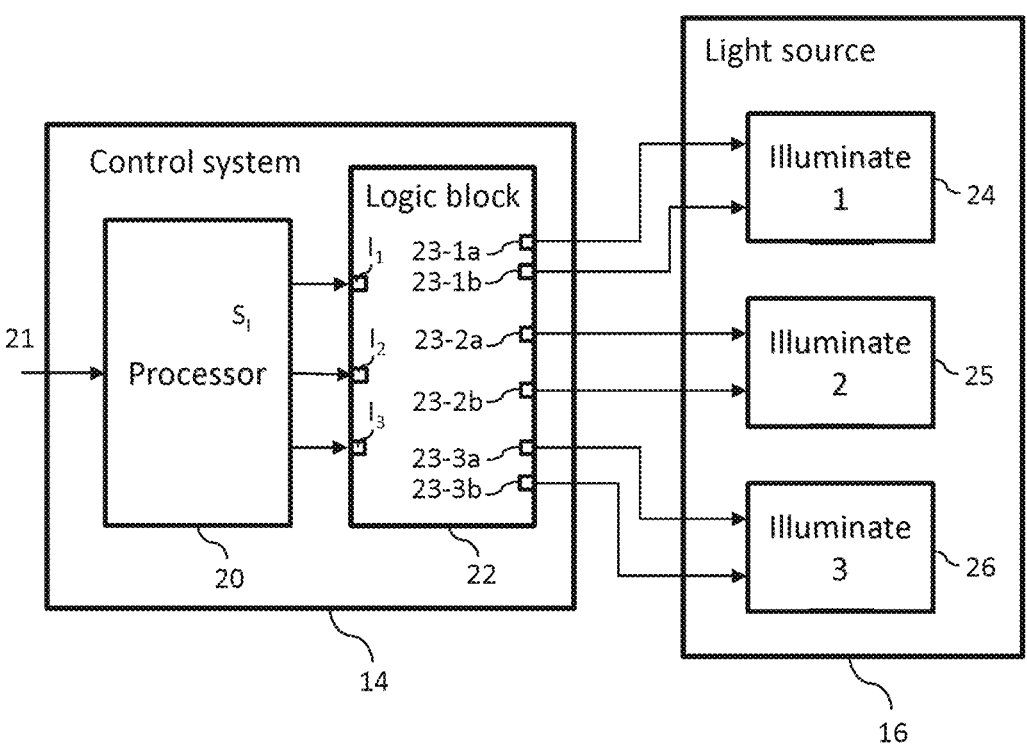
FIG. 2 is a schematic diagram of a control system according to a first example embodiment herein, and the light source of FIG. 1.

Turning now to FIG. 2, the control system 14 of the present example embodiment and the light source 16 of the ophthalmic imaging system 10 are shown schematically in further detail. The control system 14 comprises a processor 20 and a logic block 22. The control system 14 is operatively coupled to the light source 16 such that the control system 14 can control the light source 16. The light source 16 comprises N illuminates having different wavelengths, where N is an integer greater than or equal to 2. By way of an example, N=3 in the present example embodiment, and the light source 16 shown in FIG. 2 comprises a first illuminate 24 in the example form of a red laser, a second illuminate 25 in the example form of a green laser, and a third illuminate 26 in the example form of a blue laser. One or more of the illuminates 24, 25 and 26 may be provided in another form in an alternative example embodiment, for example in the form of a swept-source laser, an ultra-violet laser or an infra-red laser.

Each of the illuminates 24, 25, and 26 is independently controllable by the control system 14 such that the control system 14 can select one or more of the illuminates 24, 25, and 26 for use in imaging and determine an operating power to be set for each of the selected one or more illuminates.

The processor 20 is arranged to receive a modality identification signal 21, which is indicative of a selected imaging modality of the available imaging modalities of the ophthalmic imaging system 10, and to select, based on the modality identification signal 21, one or more of the illuminates 24, 25, and 26 that is/are to be illuminated during imaging of the eye 12 by the ophthalmic imaging system 10 in the selected imaging modality. The modality identification signal 21 may be input by a clinician operating the ophthalmic imaging system 10 via an input device (such as a keyboard, touchscreen or the like). As an alternative, the modality identification signal 21 may be input from a sub-system within the ophthalmic imaging system 10 arranged to select the imaging modality which the ophthalmic imaging system 10 should operate in.

The processor 20 may comprise a memory (not shown in FIG. 2) comprising computer-readable instructions in the form of software, which, when executed by the processor 20, cause the processor 20 to generate an input signal, $S_i$, which identifies the selected one or more illuminates from among the available illuminates 24, 25, and 26 within the light source 16. The generated input signal $S_i$ is communicated to the logic block 22.

The processor 20 is operatively coupled to the logic block 22 within the control system 14. The logic block 22 comprises logic that may be implemented, for example, by hardwired logic gates, a programmable logic array (such as a field-programmable gate array (FPGA), for example) or analogue logic. The logic block 22 is arranged to receive the input signal $S_i$ from the processor 20 that is indicative of the selection of one or more of the illuminates 24, 25 and 26 that are to be illuminated for imaging in the selected imaging modality. The input signal $S_i$ to the logic block 22 from the processor 20 identifies the selected illuminate(s) but may not contain information about the operating power of the selected illuminate(s).

In response to receiving the input signal S from the processor 20, the logic within the logic block 22 determines the respective operating power for each illuminate of the selected one or more illuminates that is/are identified by the received input signal $S_i$. As shown in FIG. 2, the logic block 22 comprises three inputs, $I_1$, $I_2$ and $I_3$, which are operatively coupled to the processor 20, wherein each of the inputs corresponds to a respective illuminate of the illuminates 24, 25 and 26 within the ophthalmic imaging system 10. More generally, the logic block 22 may comprises two or more inputs coupled to the processor 20, wherein each input corresponds to a respective illuminate of the two or more illuminates within the ophthalmic imaging system 10. Accordingly, in an alternative example embodiment, where the light source 16 comprises five illuminates the logic block 22 would have five inputs from the processor 20, each input corresponding to a respective illuminate in the light source 16. The input signal $S_i$ generated by the processor 20 identifies the selected one or more illuminates that are to be used for imaging in the selected imaging modality by comprising a respective signal transmitted to each of the inputs of the logic block 22 that correspond to the selected illuminate(s).

The logic block 22 comprises logic arranged to determine a respective operating power for each illuminate of the selected one or more illuminates, based on the received input signal $S_i$. The logic block 22 may advantageously ensure that the correct power level of each illuminate 24, 25 and 26 within the light source 16 is determined, thereby ensuring that the total power of light delivered to the patient's eye 12 is set correctly and, furthermore, is below a threshold amount. The dedicated hardware logic within the logic block 22 implements the power control logic for determining the operating power level of each illuminate 24, 25 and 26 in a reliable manner that is less susceptible to glitches or crashes that can occur from time to time whilst executing software.

The logic block 22 may comprise logic implemented by hardwired logic gates, as in the present example embodiment, or a programmable logic array made from a plurality of interconnected logic modules or logic cells, wherein each logic cell may be a configurable logic gate. The logic block 22 is configured to implement the desired logic such that the logic block 22 can receive the input signal $S_i$ from the processor 20 identifying the selection of one of more of the illuminates that are to be illuminated, and determine the respective operating power for each illuminate of the selected one or more illuminates, based on the input signal $S_i$ received from the processor 20. The logic block 22 may, as in the present example embodiment, comprise, for each of the illuminates 24, 25 and 26 within the ophthalmic imaging system 10, a respective two or more outputs arranged to output control signals for controlling an operating power of the illuminate. A control signal output from each output of the two or more outputs is arranged to set an operating power of the illuminate to a respective power level.

As shown in FIG. 2, the logic block 22 has six outputs, 23-1a, 23-1b, 23-2a, 23-2b, 23-3a and 23-3b, that are coupled to illuminates 24, 25 and 26 within the light source 16. In the example embodiment shown in FIG. 2, each of the illuminates 24, 25 and 26 is connected to two outputs from the logic block 22 such that each illuminate comprises two inputs. Each of the inputs to the respective illuminates 24, 25 and 26 may be indicative of an operating power level that illuminate should operate at. For example, one of the inputs to the respective illuminates 24, 25 and 26 may be indicative of a low-power operating mode, and the other input may be indicative of a high-power operating mode. More generally, the logic block 22 may comprise, for each illuminate within the ophthalmic imaging system 10, a respective first output, 23-1a, 23-2a or 23-3a, and a respective second output, 23-1b, 23-2b or 23-3b, wherein a control signal output from the respective first output 23-1a, 23-2a or 23-3a is arranged to set an operating power of the illuminate to a first power level, and a control signal output from the respective second output 23-1b, 23-2b or 23-3b is arranged to set an operating power of the illuminate to a second power level that is higher than the first power level.

The logic block 22 is further arranged to generate a respective control signal for each illuminate of the selected one or more illuminates, wherein each control signal indicates the respective operating power determined for the respective illuminate. The logic block 22 is further arranged to output the respective control signal to each illuminate of the selected one or more illuminates, thereby causing those illuminates to operate at the respective determined powers (power levels).

FIG. 3 is a table showing respective operating powers of illuminates 24, 25 and 26 in the light source 16 for seven example imaging modes of the ophthalmic imaging system 10. The mappings between imaging modes, selections of illuminates to be illuminated for imaging, and illuminate power levels illustrated in the table of FIG. 3 are used by the control system 14 to set the output power level of each illuminate that is required for any selected imaging modality of the available imaging modalities in the ophthalmic imaging apparatus 10. Each of the imaging modalities numbered 1 through 7 require a different selection of one or more of the illuminates 24, 25 and 26 to be illuminated within the ophthalmic imaging system 10. The table shown in FIG. 3 shows seven examples of imaging modalities for the ophthalmic imaging system 10 shown in FIG. 2, which comprises a red laser as an example of the first illuminate 24, a green laser as an example of the second illuminate 25, and a blue laser as an example of the third illuminate 26. However, the table of FIG. 3 may be changed to have fewer than, or more than, seven imaging modalities, and/or indicate power levels for other (and/or additional) types of illuminate than those shown.

In the example shown in FIG. 3, each illuminate has three operating states that it could operate in, namely: a high-power mode, a low-power mode and an off state (zero power mode). The high-power mode and the low-power mode correspond to the high- and low-power inputs to each of the illuminate 24, 25 and 26 from the logic block 22. The zero-power mode (or off state) corresponds to no input being provided to an illuminate from the logic block 22. The high-power operating mode may correspond to an operating power of between about 2 mW and 5 mW, depending on the wavelength of the illuminate. The low-power operating mode may correspond to an operating power between about 0.5 mW and 1.5 mW, depending on the wavelength of the illuminate.

As shown in FIG. 3, each imaging modality of the ophthalmic imaging system 10 corresponds to a selection of one or more of the illuminates 24, 25 and 26 that is/are to be illuminated for imaging in the respective imaging modality, which has been made by the processor 20. Furthermore, for each of the selections, a respective pre-determined power state is specified, which defines a respective operating power level to which each of the illuminates 24, 25 and 26 is to be set, such that the correct power of light is delivered to the patient's eye 12 during imaging in the selected imaging modality. The power state for each selection of one or more of illuminates shown in the table of FIG. 3 may be implemented in the logic within the logic block 22, such that, upon receipt of the input signal S$_i$, the logic within the logic block 22 can determine the operating power level to which each of the selected one or more illuminates is to be set.

For example imaging modalities 1 through 3 in FIG. 3, a single illuminate of the illuminates 24, 25 and 26 is to be illuminated. For the example imaging modalities shown in FIG. 3, for which a single illuminate is to be illuminated, the table of FIG. 3 indicates that the operating power of that illuminate is to be set to pre-set "HIGH" power level (although, in another example embodiment, the illuminate could instead be set to pre-set "LOW" power level, which is lower than the pre-set "HIGH" power level).

For example imaging modalities 4 through 6 of FIG. 3, only two of the illuminates 24, 25 and 26 are to be illuminated. For these imaging modalities, the table may, as in the example of FIG. 3, indicate that the operating power of a first of these illuminates is to be set to either the pre-set "HIGH" power level or the pre-set "LOW" power level, and that the operating power of the remaining second illuminate is to be set (independently of the operating power of the first illuminate) to either the pre-set "HIGH" power level or the pre-set "LOW" power level, the respective operating powers of the first and second illuminates depending on the requirements of the selected imaging modality.

Example imaging modality 7 in FIG. 3 requires all three of the illuminates 24, 25 and 26 to be illuminated. In the example shown, each of the illuminates 24, 25 and 26 is to be operated at an operating power which is at the pre-set "LOW" power level when all of the illuminates 24, 25 and 26 are to be illuminated. However, in another example embodiment, in the case where all three of the illuminates 24, 25 and 26 are to be illuminated, they may be all be operated at an operating power which is at the pre-set "HIGH" power level, or some of the selected illuminates may be operated at the "HIGH" power level while the remaining ones of the selected illuminates are operated at the "LOW" power level. For imaging modalities that require all three illuminates 24, 25 and 26 to be illuminated, operating the three illuminates at the pre-set "HIGH" power level would result in the total power of light being delivered to a patient's eye 12 exceeding a safe threshold power level, and is therefore avoided.

The processor 20 is arranged to receive the modality identification signal 21, which is indicative of the selected imaging modality that the ophthalmic imaging system 10 is to operate in. The processor 20 is arranged to use the modality identification signal 21, and the associations between (i) each available imaging modality, (ii) the respective selection of one or more of the illuminates 24, 25 and 26 that is/are to be used by the ophthalmic imaging system 10 when imaging the eye 12 in the selected imaging modality, and (iii) the respective operating power level(s) of the selected one or more illuminates (these associations being provided in any suitable form, such as a look-up table (LUT), which is represented pictorially in FIG. 3), to select one or more of the illuminates that is/are to be used by the ophthalmic imaging system 10 when imaging the eye 12 in the selected imaging modality.

Operations performed by the control system 14 will now be described in the context of an example in which the received modality identification signal 21 is indicative of imaging modality 4.

In this example, the processor 20 uses the modality identification signal 21 and the associations set out above to determine that the red laser and the green laser within the light source 16 are to be illuminated. The processor 20 generates an input signal S$_i$ for the logic block 22, which identifies the selected illuminates, namely the red laser and the green laser. However, the processor 20 does not provide the logic block 22 with an indication of the respective power levels at which the red laser and the green laser are to be operated at.

Furthermore, in this example, the logic block 22 receives, from the processor 20, the input signal S$_i$ in the form of respective signals that are received at the inputs of the logic block 22 corresponding to the red laser and the green laser (with no signal being received at the remaining input of the logic block 22, which corresponds to the blue laser). The logic within the logic block 22 then determines the required operating power level for each of the red laser and the green laser, using the associations set out above. More specifically, the logic within the logic block 22 determines that both the red laser and the green laser are to be operated at the pre-set "HIGH" power level. The logic block 22 then generates a first control signal for the red laser and a second control signal for the green laser, wherein the first control signal indicates the power level at which the red laser is to operate, and the second control signal indicates the power level at which the green laser is to opera. The first control signal is communicated to the red laser, in the form of a signal which is transmitted to the red laser from an output of the logic block 22 for the red laser, which output corresponds to the "HIGH" operating power level. Similarly, the second control signal is communicated to the green laser, in the form of a signal which is transmitted to the green laser from an output of the logic block 22 for the green laser, which output corresponds to the "HIGH" operating power level. In response to receiving the first control signal from the logic block 22, the red laser begins operating at the "HIGH" power level. Similarly, in response to receiving the second control signal from the logic block 22, the green laser begins operating at the "HIGH" power level. The blue laser, which does not receive a control signal from the logic block 22, remains inactive and does not generate light.

The imaging modalities 1 through 7 in the table of FIG. 3 have been provided by way of example only. Other possible imaging modalities, in which the ophthalmic imaging system 10 could operate, include, for example: a scanning laser ophthalmoscopy (SLO), SLO colour composite, autofluorescence (AF), fluorescein angiography (FA), indocyanine green angiography (ICGA) and optical coherence tomography (OCT).

Figure 4:
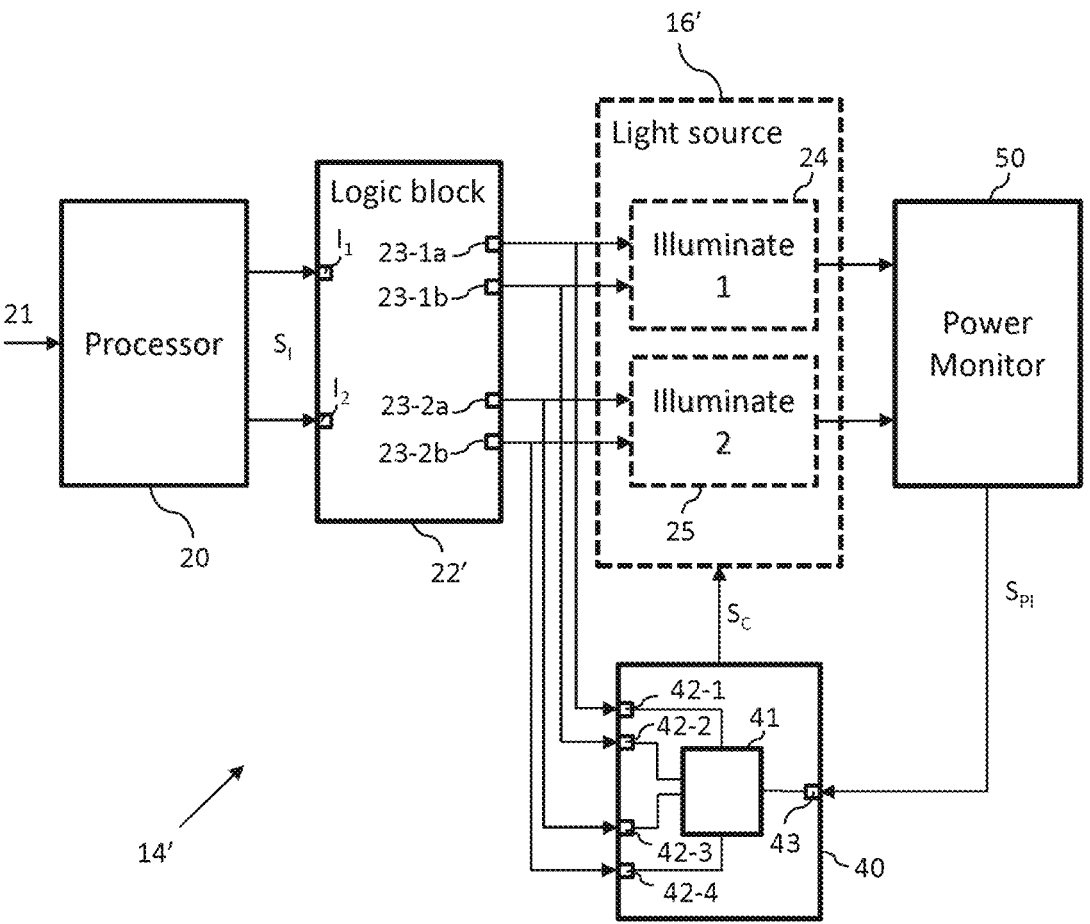
FIG. 4 is a schematic diagram of a control system according to a second example embodiment herein.

FIG. 4 is a schematic illustration of a control system 14' according to a second example embodiment, for controlling illuminates of an ophthalmic imaging system. The control system 14' shown in FIG. 4 is coupled to a light source 16' within the ophthalmic imaging system. The light source 16' comprises a first illuminate 24 in the example form of a red laser, and a second illuminate 25 in the example form of a green laser. The illuminates of the light source 16' are the same as the first illuminate 24 and the second illuminate 25 described above with reference to FIG. 2. The light source 16' is not limited to this form, however, and may alternatively comprise more than two illuminates, each of which may take any of the forms described above in relation to the first example embodiment. Furthermore, the ophthalmic imaging system, whose light source the control system 14' is arranged to control, may be the same as the ophthalmic imaging system 10 of the first example embodiment described above.

The control system 14' of FIG. 4 comprises a processor 20 and a logic block 22', which are the same as the like numbered components of the control system 14 of the first example embodiment, which have been described above with reference to FIG. 2, except that the logic block 22' is arranged to control only illuminate 24 and illuminate 25, and therefore does not have input $I_3$ or outputs 23-3a and 23-3b relating to the control of illuminate 26 shown in FIG. 2. The control system 14' further comprises an electronic safety system 40 and a power monitor 50, which will now be described in more detail.

The power monitor 50 is arranged to measure a respective power output from each of the illuminates within the ophthalmic imaging system, and to generate a power input signal, $S_{PI}$, which is indicative of the measured power outputs.

In general, the electronic safety system 40 comprises one or more first inputs, which is/are arranged to receive the power input signal $S_{PI}$ from the power monitor 50, and one or more second inputs, which is/are arranged to receive, from the logic block 22', the respective control signal generated for each illuminate of the selected one or more illuminates. The electronic safety system 40 further comprises a controller 41, which is arranged to compare, for each illuminate of the selected one or more illuminates, the respective measured power output from the illuminate with the respective operating power set for the illuminate by the control signal from the logic block 22', to determine if the measured power output from the illuminate differs from the set operating power by more than a predefined amount.

The electronic safety system 40 may, as in the present example embodiment, comprise a plurality of inputs, shown at 42-1 to 42-4 in FIG. 4, which are arranged to receive from the logic block 22' the respective control signal generated for each illuminate of the selected one or more illuminates. Each of these inputs 42-1 to 42-4 is therefore arranged to receive, from the logic block 22', a signal which is indicative of the determined operating power to be set for the corresponding illuminate of the illuminates 24 and 25 in the light source 16'. The electronic safety system 40 is further arranged to receive the power input signal $S_{PI}$ from power monitor 50, via an input 43. The power monitor 50 is arranged to measure the power output from each of the illuminates 24 and 25 within the light source 16'. For each illuminate of the illuminates 24 and 25, a dedicated power monitoring device may be provided in the power monitor 50, which is arranged to measure the power output of the illuminate. The power monitor 50 may comprise one or more photodiode power sensors or thermal power sensors, for example.

The power outputs from the illuminates 24 and 25, as measured by the power monitor 50, are input to the electronic safety system 40. The controller 41 of the electronic safety system 40 (which may be provided in the form of a processor, or logic block, for example) is arranged to compare the received measured power output from the first illuminate 24 with the determined operating power of the first illuminate 24 output from the logic block 22'. The controller 41 is further arranged to compare the received measured power output from the second illuminate 25 with the received determined operating power of the second illuminate 25 output from the logic block 22'. If, for each of the illuminates 24 and 25, the comparison between the measured power output and the determined power output indicated by the control signal results in a match (i.e. indicates that the measured power output does not differ from the determined power output by more than a predefined amount) then the illuminates 24 and 25 within the light source 16' are determined by the controller 41 to be functioning correctly. When the controller 41 of the electronic safety system 40 determines the illuminates 24 and 25 are functioning correctly, the controller 41 does not take any action and continues comparing the measured and determined power levels throughout operation of the light source 16'.

On the other hand, if the comparison made for either one of the illuminates 24 and 25 does not result in a match (i.e. indicates that the measured power output of the first illuminate 24 or the second illuminate 25 differs from the determined power output by the predefined amount or more) then the controller 41 of the electronic safety system 40 outputs a control signal Sc to the light source 16', which causes the light source 16' to turn off the illuminate for which the comparison has not resulted in a match. If neither of the illuminates 24 and 25 is thus determined by the controller 41 to be functioning correctly, the controller 41 turns off both the illuminates 24 and 25. The control signal Sc from the controller 41 of the electronic safety system 40 to the light source 16' may be a trip signal to trip the power or remove the power to the light source 16' thereby turning the illuminates 24 and 25 off. The light source 16' may comprise a shutter mechanism, and the controller 41 may be arranged to output a signal which causes the shutter mechanism to close, thereby preventing light from being conveyed to the patient's eye 12. The controller 41 may generate control signals to simultaneously close a shutter mechanism and trip the power to the light source 16'.

As shown in FIG. 4, the electronic safety system 40 has an input corresponding to each operating power level for each of the illuminates 24 and 25 in the light source 16'. In the example embodiment of FIG. 4, the electronic safety system 40 comprises four inputs 42-1 to 42-4 from the logic block 22'. For example, the inputs for each of the illuminates 24 and 25 may correspond to the "LOW" power level and the "HIGH" power level. If there were more illuminates in the light source 16' or if the illuminates had further operating power levels, then the number of inputs to the electronic safety system 40 would vary accordingly. Typically, the number of inputs to the electronic safety system 40 equals the number of outputs from the logic block 22, such that each output from the logic block 22' is input to the electronic safety system 40.

In another example embodiment, the power monitor 50 may be further arranged to measure a total power output from both the illuminates 24 and 25 in the light source 16'. In this example embodiment, the controller 41 of the electronic safety system 40 may compare the total power of illumination being output by the illuminates 24 and 25 with an expected total operating power for the selected imaging modality, which is predetermined to be at a safe level. The controller 41 may receive the input signal S$_i$ from the processor 20, which is indicative of the selected imaging modality. In this example embodiment, the controller 41 may output a signal to the light source 16' when the total power being output by the light source 16' does not match an expected total power value for the selected imaging modality. The output signal may control the power supply to the light source 16' and/or the shutter mechanism to prevent light from the illuminates 24 and 25 from reaching the patient's eye 12.

Alternatively, in another example embodiment, the power monitor 50 may be further arranged to measure a total power output from the illuminates 24 and 25 in the light source 16'. In this example embodiment, the electronic safety system 40 may not receive any signals from the logic block 22'. Instead, the controller 41 of the electronic safety system 40 may be arranged to compare the total power of illumination being output by the illuminates 24 and 25 in the light source 16' with a pre-determined threshold value. In this example embodiment, the controller 41 may output a signal to the light source 16' when the total power being output by the light source 16' exceeds the pre-determined threshold value. The output signal may be arranged to trip the power supply to the light source 16' and/or operate a shutter mechanism to turn the illuminates 24 and 25 off, as described above. The pre-determined threshold value may be a power level deemed to be a safe level of light to be delivering to the patient's eye 12.

A method of controlling two or more illuminates a multi-modality ophthalmic imaging system will now be described with reference to FIG. 5. The method is performed by a control system of the multi-modality ophthalmic imaging system, which may comprise a processor 20 and a logic block 22 as described above with reference to FIG. 2 (or a logic block 22' as described above with reference to FIG. 4).

Figure 5:
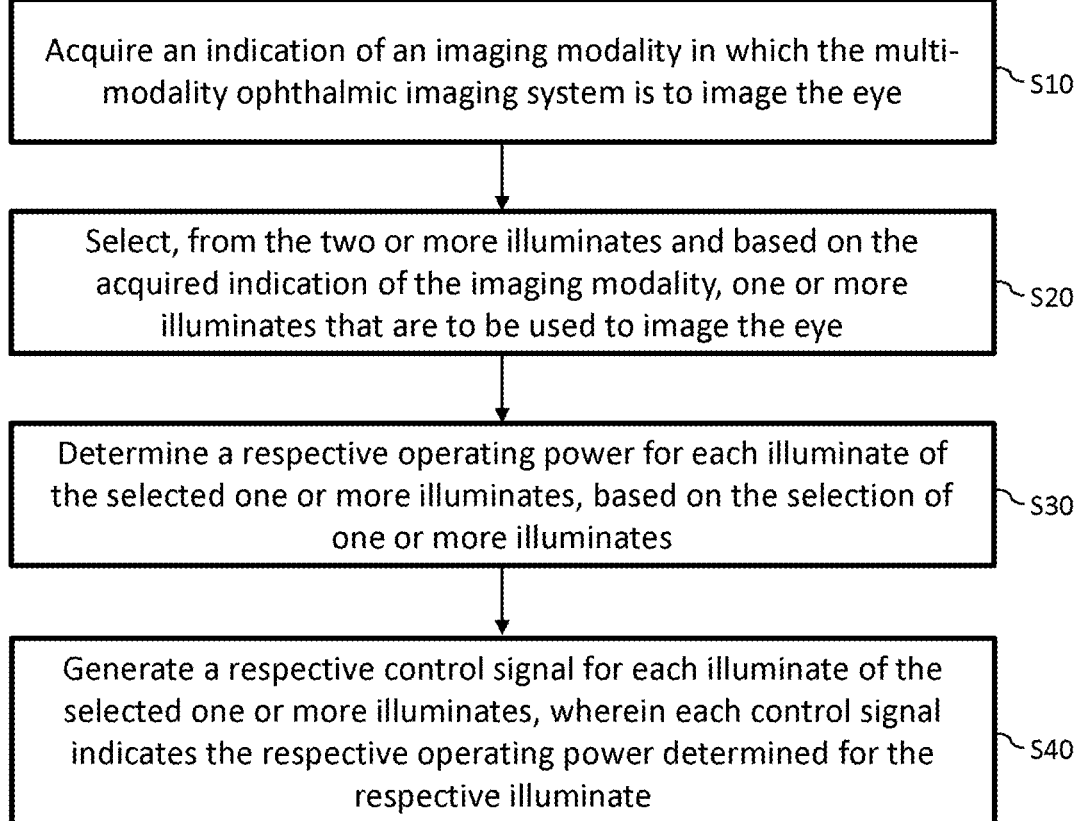
FIG. 5 is a flow chart illustrating a method of controlling illuminates within a multi-modality ophthalmic imaging system, according to an example embodiment herein.

In S10 of FIG. 5, the control system acquires an indication of an imaging modality in which the multi-modality ophthalmic imaging system is to image an eye. The imaging modality may be selected by a clinician operating the ophthalmic imaging system or automatically by the ophthalmic imaging system.

In S20 of FIG. 5, the control system selects, from the two or more illuminates, and based on the acquired indication of the imaging modality, one or more illuminates that are to be used to image the eye. Where the control system of the multi-modality ophthalmic imaging system comprises a processor 20 and a logic block 22, as described above with reference to FIG. 2, this selection may be made by the processor 20. The processor 20 may make the selection in S20 using a look-up table (LUT) of the form described above with reference to FIG. 3, for example.

In S30 of FIG. 5, the control system determines a respective operating power for each illuminate of the selected one or more illuminates, based on the selection of one or more illuminates. Where the control system of the multi-modality ophthalmic imaging system comprises the above-described processor 20 and logic block 22, S30 of FIG. 5 may be performed by logic in the logic block 22, which may be hard-wired logic, as described above. In this case, in S30 of FIG. 5, the selection of one or more illuminates made in S20 of FIG. 5 is input to the logic for determining the operating power level for each of the selected one or more illuminates, for example by inputting signals to inputs of the logic block 22 corresponding to the respective illuminates in the selection. The logic block 22 determines the operating power level of each illuminate in the selection by using an association, which is provided for each selection of illuminates of different possible selections of illuminates, between the selection of illuminates and respective operating power levels of the illuminates that are to be used for that selection of illuminates. These associations are set in the logic within the logic block 22.

In S40 of FIG. 5, the control system generates a respective control signal for each illuminate of the selected one or more illuminates, wherein each control signal indicates the respective operating power determined for the respective illuminate. Where the control system of the multi-modality ophthalmic imaging system comprises the above-described processor 20 and logic block 22, S40 of FIG. 5 may be performed by logic in the logic block 22, as described above. The control signals may be provided to the corresponding one or more selected illuminates, as described above in relation to the first example embodiment. The one or more selected illuminates respond to the received control signals by starting to operate at the respective determined operating power levels.

Where the control system comprises an electronic safety system, as described above with reference to FIG. 4, the electronic safety system may perform operations, as described in the following with reference to FIG. 6, after S40 in FIG. 5.

In S50 of FIG. 6, the electronic safety system acquires a power input signal, which is indicative of measurements of a respective power output from each of the selected one or more illuminates.

In S60 of FIG. 6, the electronic safety system compares, for each illuminate of the selected one or more illuminates, the respective measured power output from the illuminate with the respective operating power determined for the illuminate, to determine if the measured power output from the illuminate differs from the operating power determined for the illuminate by more than a predefined amount. If the electronic safety system determines in S60 that the measured power output from the illuminate does not differ from the operating power determined for the illuminate by more than the predefined amount ("NO" at S65 in FIG. 6), this indicates that the selected one or more illuminates are functioning correctly, and the electronic safety system continues to monitor the power output of the selected one or more illuminates, by looping back to S50 in FIG. 6.

However, in case the electronic safety system determines that, for at least one illuminate of the selected one or more illuminates, the measured power output from the illuminate differs from the operating power determined for the illuminate by more than the predefined amount ("YES" at S65 in FIG. 6), the process proceeds to S70 of FIG. 6, where the electronic safety system turns off the selected one or more illuminates, for example by outputting a trip signal for disconnecting a power supply to the selected one or more illuminates or by outputting a signal which causes a shutter mechanism to close a shutter at an optical output of the light source, thereby preventing light from the selected one or more illuminates from propagating to the patient's eye.

Figure 7:
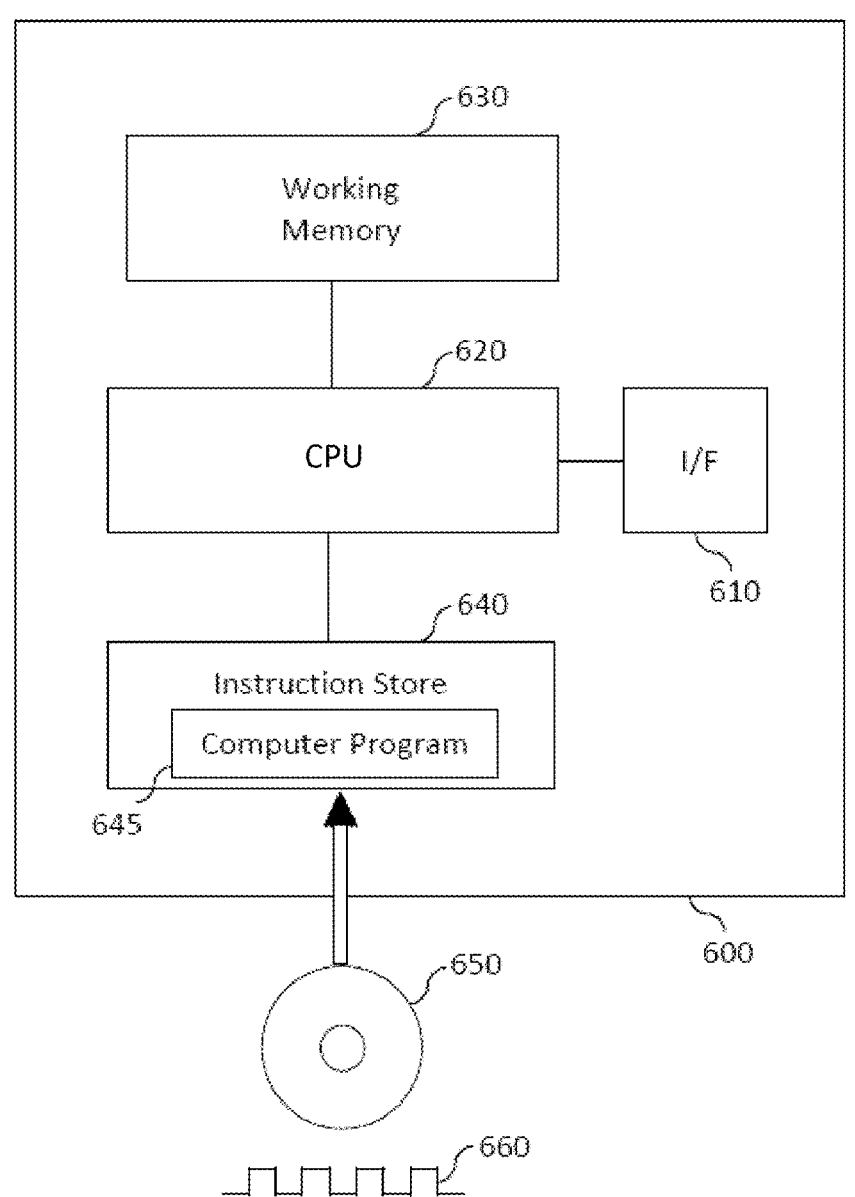
FIG. 7 is an example hardware implementation of an apparatus that can operate as a control system for an ophthalmic imaging system according to an example embodiment herein.

FIG. 7 is a schematic illustration of a programmable signal processing hardware 600, which provides an example implementation of the processor 20 of the example embodiments described above. The programmable signal processing apparatus 600 comprises a communication interface (I/F) 610, for receiving the input 21 indicative of the selected imaging modality and for outputting the determined selection of one or more illuminates to the logic block 22. The communication interface (I/F) 610 can input/output any information obtained as part of the methods described herein.

The signal processing apparatus 600 further comprises a Central Processing Unit (CPU) 620 (although an alternative processing unit may alternatively be provided, such as a Graphics Processing Unit (GPU), for example), a working memory 630 (e.g. a random access memory) and an instruction store 640 storing a computer program 645 comprising computer-readable instructions which, when executed by the CPU 620, cause the CPU 620 to perform various functions of the processor 20 described herein.

The working memory 630 stores information used by the CPU 620 during execution of a computer program, as described below. The instruction store 640 comprises, for example, a ROM (e.g. in the form of an electrically erasable programmable read-only memory (EEPROM) or flash memory) which is pre-loaded with computer-readable instructions of a computer program 45. Alternatively, the instruction store 640 comprises a RAM or similar type of memory, and the computer-readable instructions of the computer program 645 can be input thereto from a computer program product, such as a non-transitory, computer-readable storage medium 650 in the form of a CD-ROM, DVDROM, etc. or a computer-readable signal 660 carrying the computer-readable instructions. In any case, the computer program 645, when executed by the CPU 620, causes the CPU 620 to perform the above-described functions of the processor 20.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized in ways other than those shown in the accompanying figures.

Software for controlling the operation of the processor 20 presented herein may be provided as a computer program or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a processor 20 in the form of a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

The computer program product described above may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above-described example embodiments, but should be defined only in accordance with the following claims and their equivalents.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

The invention claimed is:

1. A control system for controlling two or more illuminates of a multi-modality ophthalmic imaging system that are arranged to generate light for imaging an eye, the control system comprising:

a processor controllable by software to select, from the two or more illuminates and based on a selected imaging modality of the ophthalmic imaging system, one or more illuminates that are to be used to image the eye, and to generate an input signal identifying the selected one or more illuminates; and logic hardware in communication with the processor and configured to;

receive the input signal from the processor;

generate, based on the received input signal, a respective operating power for each illuminate of the selected one or more illuminates; and generate a respective control signal for each illuminate of the selected one or more illuminates, wherein each control signal indicates the respective operating power determined for the respective illuminate.

2. The control system as claimed in claim 1, wherein:

the logic hardware comprises two or more inputs coupled to the processor, each input corresponds to a respective illuminate of the two or more illuminates within the ophthalmic imaging system, and the input signal generated by the processor identifies the selected one or more illuminates by comprising a respective signal transmitted to each of one or more inputs of the hardware that correspond to the selected one or more illuminates.

3. The control system as claimed in claim 1, wherein;

the logic hardware comprises, for each illuminate within the ophthalmic imaging system, a respective two or more outputs arranged to output control signals for controlling an operating power of the illuminate, and a control signal output from each output of the two or more outputs is arranged to set an operating power of the illuminate to a respective power level.

4. The control system as claimed in claim 3, wherein;

the logic block comprises, for each illuminate within the ophthalmic imaging system, a respective first output and a respective second output, a control signal output from the respective first output is arranged to set an operating power of the illuminate to a first power level, and a control signal output from the respective second output is arranged to set an operating power of the illuminate to a second power level which is higher than the first power level.

5. The control system as claimed in claim 1, wherein the control system further comprises:

a power monitor arranged to measure a respective power output from each of the two or more illuminates within the ophthalmic imaging system, and to generate a power input signal indicative of the measured power outputs; and an electronic safety system comprising:

one or more first inputs arranged to receive the power input signal from the power monitor;

one or more second inputs arranged to receive, from the logic hardware, block, the respective control signal generated for each illuminate of the selected one or more illuminates; and a controller arranged to compare, for each illuminate of the selected one or more illuminates, the respective measured power output from the illuminate with the respective operating power determined for the illuminate, to determine if the measured power output from the illuminate differs from the operating power determined for the illuminate by more than a predefined amount.

6. The control system as claimed in claim 5, wherein the controller is further arranged, in response to determining that the measured power output from an illuminate of the selected one or more illuminates differs from the operating power determined for the illuminate by more than the predefined amount, to generate a control signal to turn the illuminate off.

7. The control system as claimed in claim 6, wherein the controller is arranged, in response to determining that the measured power output from the illuminate of the selected one or more illuminates differs from the operating power determined for the illuminate by more than the predefined amount, to generate, as the control signal, a trip signal for disconnecting a power supply to the illuminate.

8. A multi-modality ophthalmic imaging system comprising:

two or more illuminates arranged to generate light for imaging an eye; and a control system arranged to control the two or more illuminates, the control system comprising:

a processor controllable by software to select, from the two or more illuminates and based on a selected imaging modality of the ophthalmic imaging system, one or more illuminates that are to be used to image the eye, and to generate an input signal identifying the selected one or more illuminates; and logic hardware in communication with the processor and configured to:

receive the input signal from the processor;

generate, based on the received input signal, a respective operating power for each illuminate of the selected one or more illuminates; and generate a respective control signal for each illuminate of the selected one or more illuminates, wherein each control signal indicates the respective operating power determined for the respective illuminate.

9. A method of controlling two or more illuminates of a multi-modality ophthalmic imaging system that are arranged to generate light for imaging an eye, the method comprising:

acquiring an indication of an imaging modality in which the multi-modality ophthalmic imaging system is to image the eye;

selecting, by a processor controllable by software, from the two or more illuminates and based on the acquired indication of the imaging modality, one or more illuminates that are to be used to image the eye; and generating, based on the selected one or more illuminates, an input signal to logic hardware in electrical communication with the processor, thereby causing the logic hardware to:

determine a respective operating power for each illuminate of the selected one or more illuminates, based on the input signal; and generate a respective control signal for each illuminate of the selected one or more illuminates, wherein each control signal indicates the respective operating power determined for the respective illuminate.

10. The method as claimed in claim 9, further comprising:

acquiring a power input signal indicative of measurements of a respective power output from each of the selected one or more illuminates;

comparing, for each illuminate of the selected one or more illuminates, the respective measured power output from the illuminate with the respective operating power determined for the illuminate, to determine if the measured power output from the illuminate differs from the operating power determined for the illuminate by more than a predefined amount; and in response to determining that, for at least one illuminate of the selected one or more illuminates, the measured power output from the illuminate differs from the operating power determined for the illuminate by more than the predefined amount, turning off the selected one or more illuminates.

11. The method as claimed in claim 10, wherein the selected one or more illuminates are turned off by outputting a trip signal for disconnecting a power supply to the selected one or more illuminates in response to determining that, for at least one illuminate of the selected one or more illuminates, the measured power output from the illuminate differs from the operating power determined for the illuminate by more than the predefined amount.

* * * * *